United States Patent [19]

Röhlk et al.

[11] Patent Number: 4,748,287

[45] Date of Patent: May 31, 1988

[54] PROCESS FOR THE REMOVAL OF M-DICHLOROBENZENE FROM DICHLOROBENZENE MIXTURES

[75] Inventors: Kai Röhlk, Bergisch Gladbach; Sigurd Hartung, Cologne, both of Fed. Rep. of Germany

[73] Assignee: Bayer Aktiengesellschaft, Leverkusen, Fed. Rep. of Germany

[21] Appl. No.: 920,102

[22] Filed: Oct. 16, 1986

[30] Foreign Application Priority Data

Oct. 30, 1985 [DE] Fed. Rep. of Germany ....... 3538565

[51] Int. Cl.⁴ .................... C07C 17/38; C07C 17/12
[52] U.S. Cl. .................................. 570/209; 570/208; 570/210; 570/211
[58] Field of Search ............... 570/211, 210, 209, 208

[56] References Cited

U.S. PATENT DOCUMENTS

| | | | |
|---|---|---|---|
| 1,846,727 | 2/1932 | Jaeger | 570/211 |
| 3,557,227 | 1/1971 | Fooladi | 570/210 |
| 4,089,909 | 5/1978 | Milam et al. | 260/650 R |
| 4,191,711 | 3/1980 | Lenthe et al. | 570/209 |
| 4,205,014 | 5/1980 | Potts | 570/210 |

*Primary Examiner*—J. E. Evans
*Attorney, Agent, or Firm*—Sprung Horn Kramer & Woods

[57] ABSTRACT

The invention relates to a process for the removal of m-dichlorobenzene from dichlorobenzene mixtures by chlorination in the liquid phase at elevated temperature in the presence of Friedel-Crafts catalysts, the chlorination being carried out with addition of sulphur, sulphur compounds, iodine and/or iodine compounds and the chlorination mixture then being worked up in the usual way.

12 Claims, No Drawings

PROCESS FOR THE REMOVAL OF M-DICHLOROBENZENE FROM DICHLOROBENZENE MIXTURES

BACKGROUND OF THE INVENTION

1. FIELD OF THE INVENTION

The invention relates to a process for the removal of m-dichlorobenzene from dichlorobenezene mixtures with an m-dichlorobenzene content of up to 35% by weight, relative to the total amount of dichlorobenezene in the mixture, by chlorination in the liquid phase at elevated temperature in the presence of Friedel-Crafts catalysts.

BACKGROUND INFORMATION

From U.S. Pat. No. 4,089,909, a process is known for the separation of dichlorobenzene isomers in which, in a dichlorobenzene mixture, m-dichlorobenzene is preferentially chlorinated to 1,2,4-trichlorobenzene and higher poly-chlorobenzenes with elemental chlorine in the liquid phase in the presence of Friedel-Crafts catalysts. The residual o-/p-dichlorobenzene can then be separated from higher chlorinated chlorobenzenes by conventional fractional distillation and crystallization.

In this separation process, it is disadvantageous that not only the m-dichlorobenzene in the mixture is chlorinated, but also, to a significant degree, the valuable o- and p-dichlorobenzene, as the tables in the U.S. Pat. No. 4,089,909 mentioned.

Thus, significant losses of the desired o- and p-dichlorobenzene are unavoidable during the separation and purification of the dichlorobenzene isomers according to the process described in U.S. Pat. No. 4,089,909. The economics of this process are therefore poor.

SUMMARY OF THE INVENTION

A process has now been found for the removal of m-dichlorobenzene from dichlorobenzene mixtures with an m-dichlorobenzene content of up to 35% by weight, relative to the total amount of dichlorobenzene in the mixture, by chlorination in the liquid phase at elevated temperature in the presence of Friedel-Crafts catalysts which is characterized in that the chlorination is carried out with addition of sulphur, sulphur compounds, iodine and/or iodine compounds and the chlorination mixture is then worked-up in the usual way.

DETAILED DESCRIPTION OF THE INVENTION

In the process according to the invention, dichlorozenzene mixtures as obtained in the nuclear chlorination of benzene or chlorobenzene, for example, in the liquid phase in the presence of Friedel-Crafts catalysts, can be used (cf. *Ullmanns Encyclopadie der technischen Chemie*, volume 5, page 463 and Houben-Weyl, *Methoden der organischen praparativen Chemie*, volume 5, page 653). Such dichlorobenzene mixtures contain, depending on the preparative method, about 0.5 to 3% by weight of m-dichlorobenzene and about 60 to 70% by weigth of o- and p-dichlorobenzene, the ortho/para ratio fluctuating in the range of about 3.5:1 to 1.5:1 (p-:o-dichlorobenzene). The remainder consists of unreacted benzene and monochlorobenzene as well as more highly chlorinated chlorobenzenes.

Benzene and chlorobenzene are distilled off in the usual way from the chlorination mixture obtained during the nuclear chlorination and, if necessary, the remaining dichlorobenzene mixture is subjected to a further separation by distillation. Depending on the number of separation stages, an m-dichlorobenzene-enriched dichlorobenzene mixture is obtained which contains up to 35% by weight, preferably 0.3 to 5% by weight, particularly preferably 1 to 3% by weight of m-dichlorobenzene, about 0.2 to 40% by weight, preferably 25 to 38% by weight, of o-dichlorobenzene and about 50 to 99% by weight, preferably 90 to 98% by weight, of p-dichlorobenzene. The remainder of the mixture consists of trichlorobenzenes and higher chlorinated chlorobenzenes.

The m-dichlorobenzene-enriched dichlorobenzene mixture is used in the process according to the invention as described above.

The chlorination of the dichlorobenzene mixture is usually carried out at temperatures of about 30° to 120° C., preferably 35° to 70° C.

As Friedel-Crafts catalysts, the following can, for example, be used: iron(III) chloride, aluminium chloride, zinc chloride and/or tin chloride, preferably iron(III) chloride. The amount of Friedel-Crafts catalyst to be used is not critical and usually amounts to less than 5% by weight, relative to the amount of dichlorobenzene, preferably 0.1 to 4% by weight.

In the process according to the invention, sulphur, sulphur compounds, iodine and/or iodine compounds are added to the Friedel-Crafts catalyst. As sulphur compounds, the following may be mentioned: sulphur chlorides, such as $S_2Cl_2$, iron(II) sulphide, mercaptans and thioethers; as iodine compounds, the following may be mentioned: alkyl iodides and aromatic iodine compounds. Preferably, sulphur, $S_2Cl_2$ and/or iodine are added.

The amounts of sulphur, iodine, sulphur compounds and/or iodine compounds which are added to the Friedel-Crafts catalyst are usually about 0.01 to 5% by weight, preferably 0.01 to 1% by weight, relative to the total amount of dichlorobenzene in the mixture.

The ratio of the amount of Friedel-Crafts catalyst to the amount of iodine or sulphur is about 1:1 to 5:1, preferably 1.2:1 to 3:1.

The chlorination of the dichlorobenzene mixture is conveniently continued until the m-dichlorobenzene content in the mixture lies below about 0.05% by weight, preferably about 0.02% by weight. It is however also possible to continue the chlorination, if this becomes necessary, until the m-dichlorobenzene content in the mixture lies under 0.005% by weight. m-Dichlorobenzene contents of significantly more than 0.05% by weight in the dichlorobenzene mixture are disadvantageous as the separation of the dichlorobenzene isomers is complicated by this.

In general, a slight excess of chlorine, relative to the aromatics to be chlorinated, is used in the chlorination according to the invention. About 1.0 to 1.5 moles of chlorine, preferably 1.0 to 1.05 moles of chlorine, are used per mole of the aromatics to be chlorinated.

After the chlorination is completed, the dichlorobenzene mixture obtained can be fractionally distilled to separate o- and p-dichlorobenzene.

In the process according to the invention, it is surprising that, as a result of the addition of sulphur, iodine, sulphur compound and/or iodine compounds, practically only the m-dichlorobenzene is chlorinated to higher chlorobenzenes during the chlorination of m-dichlorobenzene-enriched dichlorobenzene mixtures and that the o- and p-dichlorobenzene is hardly chlorinated any further under tbse chlorination conditions. Because of this, hardly any losses of the desired o- and p-dichlorobenzene occur. In addition, the amount of chlorine to be used in the chlorination of the mixture is reduced by the addition of sulphur, iodine, sulphur compounds and/or iodine compounds.

The following examples are intended to illustrate the process according to the invention, but without limiting it to these examples.

The example shows that p- and o-dichlorobenzene are consumed markedly during the chlorination with FeCl3 without addition of iodine or sulphur.

EXAMPLE 2

Mixture used:
73.75% of p-DClB
25.40% of o-DClB
0.35% of m-DClB
0.50% of trichlorobenzene (TriClB)

| Temp. °C. | Catalyst % by weight | Cl2 consumed % | p-DClB % | m-DClB % | o-DClB % | TriClB more highly chlorinated benzenes % |
|---|---|---|---|---|---|---|
| 50 | 0.1 FeCl3 (comparison) | 0 | 73.75 | 0.35 | 25.40 | 0.50 |
|  |  | 25 | 71.00 | 0.29 | 24.40 | 4.31 |
|  |  | 62 | 69.40 | 0.14 | 21.60 | 8.86 |
|  |  | 100 | 66.40 | 0.04 | 17.50 | 16.06 |
| 75 | 0.1 FeCl3 + (comparison) | 0 | 73.75 | 0.35 | 25.40 | 0.50 |
|  |  | 20 | 70.90 | 0.33 | 23.60 | 5.17 |
|  |  | 40 | 69.60 | 0.24 | 21.70 | 8.46 |
|  |  | 100 | 64.40 | 0.06 | 15.30 | 20.24 |
| 50 | 0.1 FeCl3 + 0.02 sulphur | 0 | 73.75 | 0.35 | 25.40 | 0.5 |
|  |  | 50 | 73.40 | 0.100 | 24.40 | 2.1 |
|  |  | 75 | 73.30 | 0.050 | 23.70 | 2.95 |
|  |  | 100 | 73.00 | 0.025 | 23.00 | 3.9 |
| 50 | 0.1 FeCl3 + 0.1 iodine | 0 | 73.75 | 0.35 | 25.40 | 0.50 |
|  |  | 33 | 72.65 | 0.18 | 23.30 | 3.9 |
|  |  | 66 | 71.50 | 0.06 | 20.70 | 7.7 |
|  |  | 100 | 70.90 | 0.023 | 19.10 | 10.0 |

EXAMPLE 1

Mixture used:
95.0% of para-dichlorobenzene (p-DClB)
4.5% of meta-dichlorobenzene (m-DClB)
0.2% of ortho-dichlorobenzene (o-DClB)
0.3% of trichlorobenzene, benzene and monochlorobenzene

| Temp. °C. | Catalyst % by weight | Cl2 consumed % | p-DClB % | m-DClB % | o-DClB % | TriClB + more highly chlorinated benzenes % |
|---|---|---|---|---|---|---|
| 55 | 0.1 FeCl3 (comparison) | 0 | 95.0 | 4.5 | 0.20 | 0.30 |
|  |  | 68 | 93.3 | 0.16 | 0.11 | 6.43 |
|  |  | 76 | 82.3 | 0.11 | 0.10 | 17.49 |
|  |  | 84 | 80.2 | 0.07 | 0.09 | 19.64 |
|  |  | 92 | 79.1 | 0.05 | 0.09 | 20.76 |
|  |  | 100 | 77.5 | 0.03 | 0.09 | 22.38 |
| 55 | 0.1 FeCl3 + 0.1 iodine | 0 | 95.0 | 4.5 | 0.20 | 0.30 |
|  |  | 100 | 92.25 | 0.02 | 0.09 | 7.64 |
| 55 | 0.1 FeCl3 + 0.05 iodine | 0 | 95.0 | 4.5 | 0.20 | 0.30 |
|  |  | 100 | 91.7 | 0.03 | 0.14 | 8.13 |
| 55 | 0.1 FeCl3 + 0.02 sulphur | 0 | 95.0 | 4.5 | 0.20 | 0.30 |
|  |  | 100 | 94.2 | 0.03 | 0.13 | 5.64 |

EXAMPLE 3

Mixture used:
55.0% of p-DClB
35.5% of o-DClB
2.8% of m-DClB
6.7% of trichlorobenzene

| Temp. °C. | Catalyst % by weight | Cl2 consumed % | p-DClB % | m-DClB % | o-DClB % | TriClB more highly chlorinated benzenes % |
|---|---|---|---|---|---|---|
| 50 | 0.1 FeCl3 | 0 | 55.0 | 2.8 | 35.5 | 6.7 |
|  |  | 100 | 43.8 | 0.03 | 13.3 | 42.87 |
| 35 | 0.2 FeCl3 + 0.08 sulphur | 0 | 55.0 | 2.8 | 35.5 | 6.7 |
|  |  | 50 | 54.5 | 0.2 | 32.5 | 12.80 |
|  |  | 100 | 54.4 | 0.02 | 30.5 | 15.08 |
| 50 | 0.02 FeCl3 + 0.008 sulphur | 0 | 55.0 | 2.8 | 35.5 | 6.7 |
|  |  | 100 | 52.4 | 0.02 | 26.7 | 20.88 |
| 50 | 0.1 FeCl3 + 0.1 iodine | 0 | 55.0 | 2.8 | 35.5 | 6.7 |
|  |  | 50 | 53.2 | 0.5 | 29.0 | 17.30 |

-continued

| Temp. °C. | Catalyst % by weight | Cl₂ consumed % | p-DClB % | m-DClB % | o-DClB % | TriClB more highly chlorinated benzenes % |
|---|---|---|---|---|---|---|
| | | 100 | 52.4 | 0.02 | 21.2 | 26.38 |

EXAMPLE 4

The chlorination was carried out in a manner corresponding to Table II of U.S. Pat. No. 4,089,909 at 66° C. The mixture used corresponded approximately to the mixture listed in Table II of the U.S. Pat. No. 4,089,909. It comprised: 0.14% by weight of benzene, 2.062% by weight of monochlorobenzene, 35.701% by weight of m-dichlorobenzene, 35.295% by weight of p-dichlorobenzene and 26.787% by weight of o-dichlorobenzene. 1000 g of the mixture were chlorinated.

| Composition of the mixture used (% by weight) | | | | | | | | |
|---|---|---|---|---|---|---|---|---|
| Benzene | MClB | m-DClB | p-DClB | o-DClB | 1,2,4-TriClB | 1,2,3-TriClB | More highly chlorinated benzenes | |
| 0.14 | 2.062 | 35.701 | 35.295 | 26.787 | — | — | | |

| Example | Catalyst | m-DClB (%) | p-DClB (%) | o-DClB (%) | 1,2,4-TriClB (%) | 1,2,3-TriClB (%) | Higher chlorinated benzenes (%) | Introduced chlorine (g) |
|---|---|---|---|---|---|---|---|---|
| 1 U.S. Pat. No. 4 089 909 | FeCl₃ (0 1%) | 0.024 | 21.99 | 3.291 | 52.427 | 8.211 | 13.994 | 450 |
| 2 | FeCl₃ (0.1%) + S (0.04%) | 0.024 | 34.997 | 20.09 | 39.618 | 3.578 | 1.655 | 245 |
| 3 | FeCl₃ (0.1%) + I₂ (0.1%) | 0.024 | 31.569 | 10.987 | 46.417 | 6.181 | 4.804 | 350 |

The example shows that p- and o-dichlorobenzene react markedly during the chlorination with FeCl₃ without addition of sulphur or iodine. In addition, a significantly greater excess of chlorine is necessary.

It will be appreciated that the instant specification and claims are set forth by way of illustration and not limitation, and that various modifications and changes may be made without departing from the spirit and scope of the present invention.

We claim:

1. In a process for the removal of m-dichlorobenzene from dichlorobenzene mixtures with a m-dichlorobenzene content of up to 35% by weight, relative to the total amount of dichlorobenzene in the mixture, by chlorination in the liquid phase at elevated temperature in the presence of a chlorine-containing Friedel-Crafts catalyst selected from the group consisting of iron(III) chloride, aluminum chloride, zinc chloride, tin chloride and mixtures thereof, the improvement comprising conducting the chlorination in the presence of an element or a compound selected from the group consisting of iodine, iodine compounds and mixtures thereof, said iodine compounds selected from the group consisting of alkyl iodides and aromatic iodides.

2. A process according to claim 1, wherein the iodine, iodine compounds or a mixture thereof is contained in amounts of 0.01 to 5% by weight, relative to the total amount of dichlorobenzene in the mixture.

3. A process according to claim 1, wherein the iodine, iodine compounds or a mixture thereof is contained in amounts of 0.01 1% by weight, relative to the total amount of dichlorobenzene in the mixture.

4. A process according to claim 1, wherein the ratio of the amount of the Friedel-Crafts catalyst to the amount of iodine is 1:1 to 5:1.

5. A process according to claim 1, wherein the ratio of the amount of the Friedel-Crafts catalyst to the amount of iodine is 1.2:1 to 3:1.

6. In a process for the removal of m-dichlorobenzene from dichlorobenzene mixtures with a m-dichlorobenzene content of up to 35% by weight, relative to the total amount of dichlorobenzene in the mixture, by chlorination in the liquid phase at elevated temperature in the presence of a chlorine-containing Friedel-Crafts catalyst selected from the group consisting of iron(III) chloride, aluminum chloride, zinc chloride, tin chloride and mixtures thereof, the improvement comprising conducting the chlorination in the presence of an element or a compound selected from the group consisting of sulphur, sulphur compounds and a mixture thereof, said sulfur compounds selected from the group consisting of sulphur chlorides, iron(II) sulphide, mercaptans and thioethers.

7. A process according to claim 6, wherein the sulphur compound is S₂Cl₂.

8. A process according to claim 6, wherein the sulphur, sulphur compounds or mixture thereof is contained in amounts of 0.01 to 5% by weight, relative to the total amount of dichlorobenzene in the mixture.

9. A process according to claim 6, wherein the sulphur, sulphur compounds or mixtures thereof is contained in amounted of 0.01 to 1% by weight, relative to the total amount of dichlorobenzene in the mixture.

10. A process according to claim 6, wherein the ratio of the amount of the Friedel-Crafts catalyst to the amount of sulphur is 1:1 to 5:1.

11. A process according to claim 6, wherein the ratio of the amount of the Friedel-Crafts catalyst to the amount of sulphur is 1.2:1 to 3:1.

12. A process according to claim 1, wherein the element is iodine.

* * * * *